(12) United States Patent
Smith (10) Patent No.: US 9,492,388 B2
(45) Date of Patent: Nov. 15, 2016

(54) COATED PARTICLES FOR SUSTAINED-RELEASE PHARMACEUTICAL ADMINISTRATION

(75) Inventor: Thomas J. Smith, Altadena, CA (US)

(73) Assignee: St. James Associates LLC/Faber Research Series, Altadena, CA (US)

( * ) Notice: Subject to any disclaimer, the term of this patent is extended or adjusted under 35 U.S.C. 154(b) by 2196 days.

(21) Appl. No.: 10/538,589

(22) PCT Filed: Dec. 22, 2003

(86) PCT No.: PCT/US03/41391
§ 371 (c)(1),
(2), (4) Date: Apr. 28, 2006

(87) PCT Pub. No.: WO2004/058223
PCT Pub. Date: Jul. 15, 2004

(65) Prior Publication Data
US 2007/0003619 A1    Jan. 4, 2007

Related U.S. Application Data

(60) Provisional application No. 60/435,163, filed on Dec. 20, 2002, provisional application No. 60/435,507, filed on Dec. 20, 2002, provisional application No. 60/435,496, filed on Dec. 20, 2002, provisional application No. 60/435,075, filed on Dec. 20, 2002, provisional application No. 60/435,423, filed on Dec. 20, 2002, provisional application No. 60/435,336, filed on Dec. 20, 2002, provisional application No. 60/435,630, filed on Dec. 20, 2002, provisional application No. 60/435,372, filed on Dec. 20, 2002, provisional application No. 60/435,106, filed on Dec. 20, 2002, provisional application No. 60/435,388, filed on Dec. 20, 2002, provisional application No. 60/435,632, filed on Dec. 20, 2002, provisional application No. 60/435,416, filed on Dec. 20, 2002, provisional application No. 60/435,557, filed on Dec. 20, 2002, provisional application No. 60/435,558, filed on Dec. 20, 2002, provisional application No. 60/435,132, filed on Dec. 20, 2002, provisional application No. 60/435,497, filed on Dec. 20, 2002, provisional application No. 60/435,494, filed on Dec. 20, 2002, provisional application No. 60/435,508, filed on Dec. 20, 2002, provisional application No. 60/435,501, filed on Dec. 20, 2002, provisional application No. 60/435,565, filed on Dec. 20, 2002, provisional application No. 60/435,038, filed on Dec. 20, 2002, provisional application No. 60/435,037, filed on Dec. 20, 2002, provisional application No. 60/435,445, filed on Dec. 20, 2002, provisional application No. 60/435,162, filed on Dec. 20, 2002, provisional application No. 60/435,338, filed on Dec. 20, 2002, provisional application No. 60/435,509, filed on Dec. 20, 2002, provisional application No.

(Continued)

(51) Int. Cl.
*A61K 9/16* (2006.01)
*A61K 9/14* (2006.01)
*A61K 9/50* (2006.01)

(52) U.S. Cl.
CPC ............ *A61K 9/146* (2013.01); *A61K 9/1688* (2013.01); *A61K 9/5026* (2013.01); *A61K 9/5084* (2013.01)

(58) Field of Classification Search
CPC ...... A61K 9/14; A61K 9/141; A61K 9/1676; A61K 9/1635; A61K 9/1647
USPC ................. 424/407, 408, 464–482, 489–496
See application file for complete search history.

(56) References Cited

U.S. PATENT DOCUMENTS

| | | |
|---|---|---|
| 2,515,898 A | 7/1950 | Rhodehamel |
| 2,627,491 A | 2/1953 | Szabo et al. |
| 3,867,519 A | 2/1975 | Michaels |
| 3,993,073 A | 11/1976 | Zaffaroni |
| 4,105,776 A | 8/1978 | Ondetti et al. |
| 4,231,938 A | 11/1980 | Monaghan et al. |
| 4,316,906 A | 2/1982 | Ondetti et al. |
| 4,337,201 A | 6/1982 | Petrillo, Jr. |
| 4,344,949 A | 8/1982 | Hoefle et al. |
| 4,346,227 A | 8/1982 | Terahara et al. |
| 4,374,829 A | 2/1983 | Harris et al. |
| 4,410,520 A | 10/1983 | Watthey |
| 4,439,196 A | 3/1984 | Higuchi |
| 4,444,784 A | 4/1984 | Hoffman et al. |
| 4,508,729 A | 4/1985 | Vincent et al. |
| 4,512,924 A | 4/1985 | Attwood et al. |
| 4,587,258 A | 5/1986 | Gold et al. |
| 4,623,588 A | 11/1986 | Nuwayser et al. |
| 4,652,441 A | 3/1987 | Okada et al. |
| 4,675,196 A | 6/1987 | Villa et al. |

(Continued)

FOREIGN PATENT DOCUMENTS

| | | |
|---|---|---|
| GB | 2 241 889 A | 9/1991 |
| JP | 61191609 U | 11/1986 |

(Continued)

OTHER PUBLICATIONS

Adams et al., Depot fluphenazine for schizophrenia, Cochrane Database Syst. Rev. 2000.

(Continued)

*Primary Examiner* — Micah-Paul Young (57) ABSTRACT

Coated microparticles for sustained-release of an active pharmaceutical ingredient after parenteral administration, and methods of producing such coated microparticles, are provided. The coated microparticles comprise core particles of an active pharmaceutical ingredient and a first polymeric coating on the core particles. The first polymeric coating is permeable to the active pharmaceutical ingredient forms a saturated solution within the coated microparticle, resulting in pseudo-zero-sustained release period. A second polymeric coating can be employed to add mechanical support or as a rate-controlling element.

28 Claims, 1 Drawing Sheet

Related U.S. Application Data

60/435,495, filed on Dec. 20, 2002, provisional application No. 60/450,722, filed on Feb. 28, 2003, provisional application No. 60/454,997, filed on Mar. 14, 2003, provisional application No. 60/435,415, filed on Dec. 20, 2002, provisional application No. 60/435,448, filed on Dec. 20, 2002, provisional application No. 60/435,449, filed on Dec. 20, 2002, provisional application No. 60/435,447, filed on Dec. 20, 2002, provisional application No. 60/435,506, filed on Dec. 20, 2002, provisional application No. 60/435,505, filed on Dec. 20, 2002.

(56) References Cited

U.S. PATENT DOCUMENTS

| | | | |
|---|---|---|---|
| 4,739,073 | A | 4/1988 | Kathawala |
| 4,757,128 | A | 7/1988 | Domb et al. |
| 4,789,724 | A | 12/1988 | Domb et al. |
| 4,857,311 | A | 8/1989 | Domb et al. |
| 4,888,176 | A | 12/1989 | Langer et al. |
| 4,897,402 | A | 1/1990 | Duggan et al. |
| 4,904,646 | A | 2/1990 | Karanewsky et al. |
| 4,906,624 | A | 3/1990 | Chucholowski et al. |
| 4,906,657 | A | 3/1990 | Roth |
| 4,920,109 | A | 4/1990 | Onishi et al. |
| 4,923,861 | A | 5/1990 | Picard et al. |
| 4,929,620 | A | 5/1990 | Chucholowski et al. |
| 4,939,143 | A | 7/1990 | Regan et al. |
| 4,940,727 | A | 7/1990 | Inamine et al. |
| 4,940,800 | A | 7/1990 | Bertolini et al. |
| 4,946,860 | A | 8/1990 | Morris et al. |
| 4,946,864 | A | 8/1990 | Prugh et al. |
| 4,950,675 | A | 8/1990 | Chucholowski |
| 4,957,940 | A | 9/1990 | Roth |
| 4,963,538 | A | 10/1990 | Duggan et al. |
| 4,968,693 | A | 11/1990 | Joshua et al. |
| 4,970,231 | A | 11/1990 | Lee et al. |
| 4,992,429 | A | 2/1991 | Ullrich et al. |
| 4,994,281 | A | 2/1991 | Muranishi et al. |
| 4,994,494 | A | 2/1991 | Regan et al. |
| 4,996,234 | A | 2/1991 | Regan et al. |
| 4,997,837 | A | 3/1991 | Chucholowski et al. |
| 5,001,128 | A | 3/1991 | Neuenschwander et al. |
| 5,001,144 | A | 3/1991 | Regan et al. |
| 5,017,716 | A | 5/1991 | Karanewsky et al. |
| 5,021,453 | A | 6/1991 | Joshua et al. |
| 5,025,000 | A | 6/1991 | Karanewsky |
| 5,081,136 | A | 1/1992 | Bertolini et al. |
| 5,091,378 | A | 2/1992 | Karanewsky et al. |
| 5,091,386 | A | 2/1992 | Kesseler et al. |
| 5,098,931 | A | 3/1992 | Duggan et al. |
| 5,102,911 | A | 4/1992 | Lee et al. |
| 5,112,857 | A | 5/1992 | Vickers |
| 5,116,870 | A | 5/1992 | Smith et al. |
| 5,130,306 | A | 7/1992 | Duggan et al. |
| 5,132,312 | A | 7/1992 | Regan et al. |
| 5,133,947 | A * | 7/1992 | Stambaugh ............... B22F 9/24 423/55 |
| 5,133,974 | A * | 7/1992 | Paradissis et al. .......... 424/480 |
| 5,135,935 | A | 8/1992 | Alberts et al. |
| 5,166,171 | A | 11/1992 | Jendralla et al. |
| 5,182,298 | A | 1/1993 | Helms et al. |
| 5,196,440 | A | 3/1993 | Bertolini et al. |
| 5,202,327 | A | 4/1993 | Robl |
| 5,250,435 | A | 10/1993 | Cover et al. |
| 5,256,689 | A | 10/1993 | Chiang |
| 5,260,332 | A | 11/1993 | Dufresne |
| 5,262,435 | A | 11/1993 | Joshua et al. |
| 5,271,946 | A * | 12/1993 | Hettche ....................... 424/490 |
| 5,273,995 | A | 12/1993 | Roth |
| 5,276,021 | A | 1/1994 | Karanewsky et al. |
| 5,283,256 | A | 2/1994 | Dufresne et al. |
| 5,286,497 | A * | 2/1994 | Hendrickson et al. ....... 424/490 |
| 5,286,895 | A | 2/1994 | Harris et al. |
| 5,302,604 | A | 4/1994 | Byrne et al. |
| 5,310,572 | A * | 5/1994 | Woodard ............. A61K 9/2813 424/468 |
| 5,317,031 | A | 5/1994 | MacConnell et al. |
| 5,356,896 | A | 10/1994 | Kabadi et al. |
| 5,369,125 | A | 11/1994 | Berger et al. |
| 5,378,475 | A | 1/1995 | Smith et al. |
| 5,385,932 | A | 1/1995 | Vickers |
| 5,618,563 | A | 4/1997 | Berde et al. |
| 5,622,985 | A | 4/1997 | Olukotun et al. |
| 5,639,480 | A | 6/1997 | Bodmer et al. |
| 5,651,990 | A | 7/1997 | Takada et al. |
| 5,654,009 | A * | 8/1997 | Hata et al. .................... 424/490 |
| 5,700,485 | A | 12/1997 | Berde et al. |
| 5,753,234 | A * | 5/1998 | Lee et al. .................... 424/204.1 |
| 5,922,340 | A | 7/1999 | Berde et al. |
| 6,046,187 | A | 4/2000 | Berde et al. |
| 6,120,787 | A * | 9/2000 | Gustafsson .......... A61K 9/1647 424/426 |
| 6,214,387 | B1 | 4/2001 | Berde et al. |
| 6,238,702 | B1 | 5/2001 | Berde et al. |
| 6,326,020 | B1 | 12/2001 | Kohane et al. |
| 6,426,339 | B1 | 7/2002 | Berde et al. |

FOREIGN PATENT DOCUMENTS

| | | |
|---|---|---|
| JP | 01311024 A | 12/1989 |
| WO | WO-98/13027 A1 | 4/1998 |
| WO | WO-02/28371 A1 | 4/2002 |

OTHER PUBLICATIONS

Arnsten et al., Antiretroviral therapy adherence and viral suppression in HIV-infected drug users: comparison of self-report and electronic monitoring, Clin. Infect. Dis., 2001, pp. 1417-1423, 33(8).

Bartlett et al., Management of Anthrax, Clinical Infectious Diseases, 2002, pp. 851-858, 35.

Blauw et al., Stroke statins and cholesterol, a meta-analysis of randomized, placebo-controlled, double-blind trials with HMG-CoA reductase inhibitors, Stroke 1997, pp. 946-950, 28(5).

Burch et al., Current indications for ACE inhibitors and HOPE for the future, Am. J. Mang. Care, 2002, pp. 478-490, quiz 491-3, 8(5).

Byron et al., Effects of heat treatment on the permeability of polyvinyl alcohol films to a hydrophilic solute, J. Pharm. Sci., 1987, pp. 65-67, 76(1).

Cadorniga et al., In vitro evaluation of the dissolution rate of crystalline suspensions destined to intramuscular administration, Eur. J. Drug Metab. Pharmacokinet, 1991, pp. 379-384, Spec. No. 3.

Cushenberry et al., Potential use of HMG-CoA reductase inhibitors for osteoporosis, Ann. Pharmacother, 2002, pp. 671-678, 36(4).

Dechend et al., Modulating angiotensin II-induced inflammation by HMH Co-A reductase inhibition, Am. J. Hypertens., 2001, pp. 55S-61S, 14(6 Pt2).

Endres et al., Stroke protection by 3-hydroxy-3-methylglutaryl (HMG)-CoA reductase inhibitors mediated by endothelial nitric oxide synthase, Proc. Nat. Acad. Sci. USA, 1998, pp. 8880-8885, 95.

Fassbender et al., Effects of statins on human cerebral cholesterol metabolism and secretion of alzheimer amyloid peptide [in process citation], Neurology, 2002, pp. 1257-1258, 59(8).

Fleckenstein, History of calcium antagonists, Cir. Res./Suppl. 1, 1983, pp. I-3-I-16, 52(2).

Friedlander et al., Postexposure prophylaxis against experimental inhalation anthrax, J. Infect. Dis., May 1993, pp. 1239-1243, 167(5).

Gharabawi et al., Enhanced psychiatric and neurological outcomes in chronically psychotic patients treated for a year with long-acting, injectable risperidone, Proc. Ann. Meeting Am. College of Neuropsychopharmacology, 2002, San Juan PR.

Houghton, Angiotensin II receptor antagonists in chronic heart failure: where to they fit?, Drugs, 2002, pp. 1433-1440, 62(10).

Jefferds et al., Adherence to antimicrobial inhalational anthrax prophylaxis among postal workers, Emerging Infectious Diseases, 2002, pp. 1138-1144, 8(10).

(56) References Cited

OTHER PUBLICATIONS

Kaplan et al., Pharmacokinetics of benzathine penicillin G: serum levels during the 28 days after intramuscular injection of 1,200,000 units., J. Pediatr., 1989, pp. 146-150, 115(1).

McCall et al., Calcium entry blocking drugs: Mechanisms of action, experimental studies and clinical uses, Curr. Probl. Cardiol., 1985, pp. 1-80.

Mimran et al., Angiotensin II receptor antagonists and hypertension, Clin. Exp. Hypertens., 1999, pp. 847-858, 21(5-6).

Mollmann et al., Clinical and pharmacologic aspects of various betamethasone crystalline suspensions, fortschr. Med., 1977, pp. 972-978, 95(14).

Nichols, Hormones and hormone antagonists, Remington: The Science and Practice of Pharmacy, 2000, p. 1371.

O'Keefe et al., Should an angiotensin-converting enzyme inhibitor be standard therapy for patients with atherosclerotic disease?, J. Am. Coll. Cardiol., pp. 1-8, 37(1).

Perico et al., Angiotensin II receptor antagonists and treatment of hypertension and renal disease, Curr. Opin. Nethrol. Hypertens., 1998, pp. 571-578, 7(5).

Quraishi et al., Depot haloperidol decanoate for schizophrenia, Cochrane Database Syst. Rev. 2000.

Remington: The Science and Practice of Pharmacy, p. 963, 19th Edition.

Table 16-1, Remington: The Science and Practice of Pharmacy, 2000, p. 209, 20th Ed.

Wong et al., Nonpeptide angiotensin II receptor antagonists I. Pharmacological characterization of 2-n-butyl-4-chloro-1-(2-chlorobenzyl)imidazole-5-acetic acid, sodium salt (S-8307), J. Pharmacol. Exp. Ther., 1988, pp. 1-7, 247(1).

Subhaga, C.S. et al., "Evaluation of an aliphatic polyurethane as a microsphere matrix for sustained theophylline delivery," J. Microencapsulation, 1995, vol. 12, No. 6, 617-625.

Supplementary European Search Report dated Apr. 14, 2011 for corresponding European Patent Application No. 03800247.3.

\* cited by examiner

COATED PARTICLES FOR SUSTAINED-RELEASE PHARMACEUTICAL ADMINISTRATION

BACKGROUND OF THE INVENTION

1. Field of the Invention

The invention relates to the field of pharmacology and, in particular, to sustained-release particles for parenteral administration of active pharmaceutical ingredients. The invention also relates to methods for preparing such particles containing an active pharmaceutical ingredient.

2. Description of the Related Art

In certain situations, it is desired that a pharmaceutical agent be administered in a sustained-release formulation, often to achieve a nearly constant or pseudo-zero-order release rate over a significant period of time and to reduce the problems associated with previous administration methods. By way of non-limiting example, such problems include poor bioavailability, first pass metabolism, non-compliance or non-adherence to therapy, and reducing the opportunity for sequestering drug tablets for illegal use. For example, the production and use of pharmaceutical preparations including larger drug particles to sustain delivery have been described in the art for certain antibiotics, insulin, and steroids (see, e.g., Ansel, Allen and Popovich, eds., *Pharmaceutical Dosage Forms and Drug Delivery Systems*, 7$^{th}$ Edition, Lippincott Williams & Wilkins, Philadelphia, Pa., 1999; Gennaro ed., *Remington: The Science and Practice of Pharmacy*, 19th Edition, Lippincott Williams & Wilkins, Philadelphia, Pa., 1995)).

Most sustained release systems employ a finely milled or micronized preparation of the active pharmaceutical ingredient as a starting point in the formulations. The release of the active pharmaceutical ingredient into the body is then controlled using matrices, membranes or other inactive ingredients or devices. Examples of methods and devices known in the art for sustained release formulations include liposomes, bioerodable matrices (e.g., PLA/PGLA matrices), drug-permeable implants (e.g., U.S. Pat. No. 3,993,073 to Zaffaroni), implants with drug-permeable and drug-impermeable membranes (e.g., U.S. Pat. No. 5,378,475 to Smith et al.), and osmotic drug delivery systems (e.g., U.S. Pat. No. 4,439,196 to Higuchi).

Penicillin G and V have been formulated as a sustained release injection by complexing the penicillin molecule with procaine or with benzathine. Suspensions of crystals of benzathine and procaine penicillin can be useful in the treatment of rheumatic fever and other infections. Typically, therapeutic levels of these antibiotics can be sustained for 14-28 days after a single IM injection (Cadorniga et al. (1991), *Eur. J. Drug Metab. Pharmacokinet.* 3:379-84; Kaplan et al. (1989), *J. Pediatr.* 115(1):146-50; U.S. Pat. No. 2,627,491; U.S. Pat. No. 2,515,898). These formulations are based on large particles of the insoluble penicillin salts which dissolve slowly over approximately two weeks. However, because delivery from these sustained release formulations is first-order the drug levels achieved at the end of the treatment period are significantly less than those achieved at the beginning of treatment.

An effort has also been made using matrix technology to achieve a sustained release injectable formulation for the drug risperidone which lasts several weeks. In addition there are sustained release preparations for other antipsychotic drugs, including decanoate esters of perphenazine and haloperidol.

There remains, however, a need in the art for improved methods for the parenterally administrable sustained-release formulations of active pharmaceutical ingredients.

SUMMARY OF THE INVENTION

The present invention depends, in part, upon the development of coated microparticles which permit the release of an active pharmaceutical ingredient over an extended or sustained-release period of time after parenteral administration. Significantly, the coated microparticles of the invention provide for sustained-release with improved kinetics, including approximately constant or pseudo-zero-order kinetics, over the sustained-release period.

In one aspect, the inventions provides a pharmaceutical preparation for sustained-release of an active pharmaceutical ingredient after parenteral administration which includes a multiplicity of coated microparticles which include the active pharmaceutical ingredient, and a first polymeric coating formed from a first polymer-forming solution. The active pharmaceutical ingredient forms a saturated solution within the coated microparticles after administration, and the first polymeric coating is permeable to the active pharmaceutical ingredient during the sustained-release period from administration of the microparticles until the concentration of the active pharmaceutical ingredient contained within the microparticles is unsaturated.

In another aspect, the invention provides coated microparticles which further include a second polymeric coating on the first polymeric coating, wherein the second polymeric coating is formed from a second polymer-forming solution and is permeable to the active pharmaceutical ingredient during the sustained-release period.

In another aspect, the invention provides coated microparticles which further include a porous second polymeric coating on the first polymeric coating, wherein the second polymeric coating is formed from a second polymer-forming solution, wherein the second polymeric coating defines pore regions which permit fluid communication between a pore portion of the first polymeric coating and the external environment, thereby allowing diffusion of the active pharmaceutical ingredient across the first polymeric coating in the pore regions, and wherein the second polymeric coating defines non-pore regions which prevent fluid communication between a non-pore portion of the first polymeric coating and the external environment, thereby inhibiting diffusion of the active pharmaceutical ingredient across the first polymeric coating in the non-pore regions. In some embodiments, the second polymeric coating is substantially impermeable to the active pharmaceutical ingredient in said non-pore regions. In addition, in some embodiments, the second polymer-forming solution includes pore-forming agents which dissolve to produce the pore regions after formation of the second polymeric coating.

In another aspect, the invention provides methods of sustained-release administration of an active pharmaceutical ingredient by administering parenterally a pharmaceutical preparation of the coated microparticles of the invention. In some embodiments, the pharmaceutical preparation is in the form of a suspension of the coated microparticles in a pharmaceutically acceptable carrier. In some embodiments, parenteral administration is subcutaneous, intravenous, intramuscular or intraocular injection.

In another aspect, the invention provides methods for producing a pharmaceutical preparation for sustained-release of an active pharmaceutical ingredient after parenteral administration. In this aspect, the methods include forming core particles including the active pharmaceutical ingredient, and forming a first polymeric coating on the core particles from a first polymer-forming solution, wherein the active pharmaceutical ingredient forms a saturated solution within the coated microparticles after administration, and wherein the first polymeric coating is permeable to the active pharmaceutical ingredient during a sustained-release period from administration of the microparticles until the concentration of the active pharmaceutical ingredient contained within the microparticles is unsaturated.

In another aspect, the methods further include the step of forming a second polymeric coating on the first polymeric coating from a second polymer-forming solution, wherein the second polymeric coating is permeable to the active pharmaceutical ingredient during the sustained-release period.

In another aspect, the methods further include the step of forming a porous second polymeric coating on the first polymeric coating from a second polymer-forming solution, wherein the second polymeric coating defines pore regions which permit fluid communication between a pore portion of the first polymeric coating and the external environment, thereby allowing diffusion of the active pharmaceutical ingredient across the first polymeric coating in the pore regions, and wherein the second polymeric coating defines non-pore regions which prevent fluid communication between a non-pore portion of the first polymeric coating and the external environment, thereby inhibiting diffusion of the active pharmaceutical ingredient across the first polymeric coating in the non-pore regions. In some embodiments, the second polymeric coating is substantially impermeable to the active pharmaceutical ingredient in the non-pore regions. In addition, in some embodiments, the second polymer-forming solution comprises pore-forming agents which dissolve to produce the pore regions after formation of the second polymeric coating.

In some embodiments, diffusion of the active pharmaceutical ingredient across the first polymeric coating exhibits pseudo-zero-order kinetics during the sustained-release period.

In some embodiments, the first polymeric coating is substantially degraded after the sustained-release period. In addition, in some embodiments, the first polymeric coating maintains structural integrity during the sustained-release period.

In some embodiments, the microparticles have a maximum dimension between 20 μm and 800 μm, between 40 μm and 400 μm, or between 100 μm and 250 μm.

In some embodiments, the active pharmaceutical ingredient is substantially insoluble in the first polymer-forming solution. In some embodiments, the active pharmaceutical ingredient is hydrophobic and the first polymer-forming solution is hydrophilic. In other embodiments, the active pharmaceutical ingredient is hydrophilic and the first polymer-forming solution is hydrophobic.

In some embodiments, the first polymeric coating and/or the second polymeric coating includes a material selected from the group consisting of naturally occurring polymers, including carbohydrates such as sugar phosphates, alkylcelluloses (e.g., ethylcellulose), and hydroxyalkylcelluloses (e.g., hydroxypropylcellulose); and synthetic polymers or co-polymers, including one or more of the following monomers: lactic acid, glycolic acid, β-propiolactone, β-butyrolactone, γ-butyrolactone, pivalolactone, α-hydroxy butyric acid, α-hydroxyethyl butyric acid, α-hydroxy isovaleric acid, α-hydroxy-β-methyl valeric acid, α-hydroxy caproic acid, α-hydroxy isocaproic acid, α-hydroxy heptanic acid, α-hydroxy octanic acid, α-hydroxy decanoic acid, α-hydroxy myristic acid, α-hydroxy stearic acid, α-hydroxy lignoceric acid, β-phenol lactic acid and polyvinyl alcohol.

In some embodiments, the first polymeric coating is applied to the core particles by an air suspension technique. In other embodiments, first polymeric coating is applied to the core particles by a dip coating technique.

In some embodiments, the weight of the polymeric coating(s) is between 0.1% and 200% of the weight of the core particle. In other embodiments, the weight of the polymeric coating(s) is between 2% and 60% of the weight of the core particle.

In some embodiments, the volume of the polymeric coating(s) is between 0.1% and 200% of the volume of the core particle. In other embodiments, the volume of the polymeric coating(s) is between 2% and 60% of the volume of the core particle.

These and other embodiments and advantages of the present invention will be apparent to one of skill in the art from the following detailed description of the invention and certain embodiments and examples.

BRIEF DESCRIPTION OF THE DRAWINGS

The following drawing is illustrative of embodiments of the invention and is not meant to limit the scope of the invention as encompassed by the claims.

DETAILED DESCRIPTION

The patent, scientific and medical publications referred to herein establish knowledge that was available to those of ordinary skill in the art at the time the invention was made. The entire disclosures of the issued U.S. patents, published and pending patent applications, and other references cited herein are hereby incorporated by reference.

DEFINITIONS

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent or later-developed techniques which would be apparent to one of skill in the art. In addition, in order to more clearly and concisely describe the subject matter which is the invention, the following definitions are provided for certain terms which are used in the specification and appended claims.

Microparticle. As used herein, the term "microparticle" means a particle having mean dimension less than 1 mm. Although the microparticles of the invention are substantially spherical in some embodiments, the microparticles can be any solid geometric shape which is not inconsistent with the principles of the invention, including, without limitation, ellipsoids, cylinders, polyhedrons and irregular shapes.

Active Pharmaceutical Ingredient. As used herein, the term "active pharmaceutical ingredient" means any compound which has utility as a pharmaceutical or drug, including, without limitation, naturally occurring compounds (e.g., hormones) and synthetic drugs.

Core Particle. As used herein, the term "core particle" means a particle comprising the active pharmaceutical ingredient of the invention and which is substantially surrounded or enveloped by the first polymeric coating. The core particle can further comprise other compounds, including, without limitation, binders, buffers, antioxidants, excipients, and additional active pharmaceutical ingredients. The core particle can be a single large crystal, a multiplicity of crystals, amorphous or non-crystalline material, glassy or hyaline material, or mixtures of the above.

Sustained Release. As used herein, the term "sustained-release" means continued release of a compound from a reservoir or source over a period of time.

Parenteral Administration. As used herein, the term "parenteral administration" means introduction of a pharmaceutical preparation into the body by a route other than the alimentary canal or digestive tract, including, without limitation, subcutaneous, intravenous, intramuscular and intraocular injection as well as surgical implantation.

Polymeric Coating. As used herein, the term "polymeric coating" means any coating which is formed by polymerization of one or more monomers to form linear or branched or cross-linked macromolecules. The coating may be variously characterized as a coating, layer, membrane, shell, capsule, or the like, and must substantially surround or envelope the core particles of the invention.

Polymer-Forming Solution. As used herein, the term "polymer-forming solution" means a solution including one or more monomers and which is capable of forming a polymeric coating. The polymer-forming solution optionally can include one or more solvents which prevent polymerization such that polymerization occurs after removal of the solvents(s). Additionally or in the alternative, the polymer-forming solution optionally can include catalysts or cross-linking agents such that polymerization occurs after removal of solvent(s), heating, or exposure to light or other radiation. The polymer-forming solution also can optionally include pore-forming agents.

Permeable. As used herein, the term "permeable" means allowing passage of molecules by diffusion but not by fluid flow.

Semi-Permeable. As used herein, the term "semi-permeable" means permeable to some molecules but not to others. As used herein, semi-permeable polymeric coatings are permeable to at least water and the active pharmaceutical ingredient within the coated microparticles of the invention.

Biocompatible. As used herein, the term "biocompatible" means characterized by not causing a toxic, injurious or immunological response when brought into contact with living tissue, particularly human or other mammalian tissue.

Biodegradable. As used herein, the term "biodegradable" means capable of partially or completely dissolving or decomposing in living tissue, particularly human or other mammalian tissue. Biodegradable compounds can be degraded by any mechanism, including, without limitation, hydrolysis, catalysis and enzymatic action.

Substantially Degraded. As used herein with respect to polymeric coatings, the term "substantially degraded" means degraded to the degree that approximately 50% of the chemical bonds resulting from polymerization of the polymer-forming solution to form the polymeric coating have been broken.

Structural Integrity. As used herein with respect to the first polymeric coating of the invention, the term "structural integrity" means retaining a continuous surface which is semi-permeable and permits diffusion, but does not include any discontinuities which permit fluid flow.

External Environment. As used herein, the term "external environment" means the local area or region of tissue surrounding the coated microparticles of the invention after parenteral administration.

Saturated. As used herein, the term "saturated" means containing the maximum concentration of a solute (e.g., an active pharmaceutical ingredient) that can be dissolved at a given temperature.

Substantially Insoluble. As used herein, the term "substantially insoluble" means having a solubility of less than 1 part solute per 1000 parts solvent by weight.

Hydrophobic. As used herein, the term "hydrophobic" means having lower affinity for an aqueous solvent than an organic solvent.

Hydrophilic. As used herein, the term "hydrophilic" means having lower affinity for an organic solvent than an aqueous solvent.

Pseudo-Zero-Order Kinetics. As used herein, the term "pseudo-zero-order kinetics" means sustained-release of the active pharmaceutical ingredient which exhibits kinetics which is zero-order (i.e., independent of concentration) or between zero-order and first-order (i.e., proportional to concentration) kinetics over the sustained-release period, where the concentration is based on the total amount of the active pharmaceutical ingredient contained within the coated microparticles. In some embodiments, the release of the active pharmaceutical ingredient exhibits kinetics which are more closely approximate zero-order than first-order kinetics.

Numerical Ranges. As used herein, the recitation of a numerical range for a variable is intended to convey that the invention may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values≥0 and ≤2 if the variable is inherently continuous.

Or. As used herein, unless specifically indicated otherwise, the word "or" is used in the "inclusive" sense of "and/or" and not the "exclusive" sense of "either/or."

Sustained Release by Coated Microparticles.

The present invention depends, in part, upon the development of coated microparticles which permit the release of an active pharmaceutical ingredient over an extended period of time after parenteral administration. Significantly, the coated microparticles of the invention provide for sustained-release with improved kinetics, including approximately constant or pseudo-zero-order kinetics, over the extended period.

Without being bound to any particular theory of the invention, it is believed that the diffusion of bodily fluids into the coated microparticles creates a saturated solution of the active pharmaceutical ingredient within the microparticles which acts as a "source" of relatively constant concentration. Similarly, because of diffusion of the active pharmaceutical ingredient away from the site of administration, into the systemic circulation, and throughout the body, the tissue surrounding the site of administration acts as a "sink" of relatively constant lower concentration. Thus, the rate of diffusion from the source to the sink remains relatively constant, and approximately linear or pseudo-zeroorder kinetics of administration can be achieved until the concentration of the active pharmaceutical ingredient within the microparticle decreases to below saturation.

The coated microparticles of the invention comprise a core including the active pharmaceutical ingredient, which is encapsulated or coated by a first polymeric coating. The first polymeric coating must be semi-permeable so as to permit the diffusion of water and the active pharmaceutical ingredient across the coating, but must not permit the bulk movement of the active pharmaceutical ingredient by fluid flow into the surrounding tissues. In addition, the first polymeric coating must remain permeable to the active pharmaceutical ingredient during a sustained-release period from administration of the microparticles until the concentration of the active pharmaceutical ingredient contained within the microparticle is unsaturated.

If the active pharmaceutical ingredient and the first polymer-forming solution are both hydrophobic or hydrophilic, the core particle may partially or completely dissolve in the polymer-forming solution, resulting in microparticles in which the active pharmaceutical ingredient is interspersed or embedded in a matrix of the polymer as opposed to being coated by the polymer. Depending upon the degree of dissolution, such microparticles may not exhibit pseudo-zero-order kinetics of release in accordance with the invention. Therefore, in some embodiments, a first polymeric coating can be employed which is formed from a first polymer-forming solution in which the active pharmaceutical ingredient is substantially insoluble.

In some embodiments, the diffusion of the active pharmaceutical ingredient across the first polymeric coating exhibits pseudo-zero-order kinetics during the sustained-release period. In some embodiments, the first polymeric coating is substantially degraded after the sustained-release period. In some embodiments, the first polymeric coating maintains structural integrity until after the sustained-release period.

The coated microparticles of the present invention can be formulated into pharmaceutical preparations for parenteral administration. For purposes of manufacturing, storage and distribution, the coated microparticles can be formulated as dry preparations. For purposes of administration, however, the coated microparticles are suspended in a pharmaceutically acceptable carrier (e.g., water, saline solution, Ringer's solution). In some embodiments the administration will be by injection (e.g., subcutaneous, intravenous, intramuscular, intraocular), although the coated microparticles can also be introduced to an open wound site or during surgery (e.g., lavage or irrigation of a wound or surgical site).

When preparing the coated microparticles of the invention, a core particle comprising the active pharmaceutical ingredient is coated with a first polymer-forming solution which forms the first polymeric coating. The first polymeric coating can be formed by any methods known in the art, as discussed in detail below. To avoid the problems of the prior art, however, it is desirable to reduce or minimize the dissolution of the active pharmaceutical ingredient in the first polymer-forming solution and the consequent formation of a polymeric coating with the active pharmaceutical ingredient interspersed with the polymeric material. Therefore, in some embodiments, the active pharmaceutical ingredient is substantially insoluble in the first polymer-forming solution. For example, in some embodiments, the active pharmaceutical ingredient is hydrophobic and the first polymer-forming solution is hydrophilic, whereas, in other embodiments, the active pharmaceutical ingredient is hydrophilic and the first polymer-forming solution is hydrophobic.

In some embodiments, the coated microparticles comprise a second polymeric coating, which is formed from a second polymer-forming solution, and which substantially surrounds or envelopes the first polymeric coating and core particle. Such second polymeric coating can serve several purposes. First, if the first polymeric coating is structurally weak or is subject to tearing or rupture during parenteral administration, a second polymeric coating can be used to add mechanical support. This objective can be accomplished by employing a second-polymeric coating which is permeable to the active pharmaceutical ingredient, or which is impermeable to the active pharmaceutical ingredient but includes pores through which the first polymeric-coating is in fluid communication with the surrounding fluid environment. Second, if the permeability of the first polymeric coating to the active pharmaceutical ingredient is too high and, therefore, results in release kinetics which are too fast, a second polymeric coating can be used to reduce the rate of release. This objective can be accomplished by employing a second-polymeric coating which is either less permeable to the active pharmaceutical ingredient, or which is impermeable to the active pharmaceutical ingredient but includes pores through which the first polymeric-coating is in fluid communication with the surrounding fluid environment.

Moreover, many active pharmaceutical ingredients and many commonly-used polymer-forming solutions are hydrophobic in nature. As a result, core particles of such active pharmaceutical ingredients tend to dissolve in many commonly-used polymer-forming solutions if the solutions are applied directly, resulting in microparticles in which the active pharmaceutical ingredient is interspersed or embedded in a matrix of the polymer as opposed to being coated by the polymer. Depending upon the degree of dissolution, such microparticles may not exhibit pseudo-zero-order kinetics of release. Therefore, a first polymeric coating can be employed which is formed from a hydrophilic first polymer-forming solution in which the active pharmaceutical ingredient is substantially insoluble. A second polymeric coating formed from a hydrophobic second polymer-forming solution can then be employed without dissolving the active pharmaceutical ingredient. Conversely, for hydrophilic active pharmaceutical ingredients, a first polymeric coating can be formed from a hydrophobic first polymer-forming solution followed by a second polymeric coating formed from a hydrophilic second polymer-forming solution.

Thus, in some embodiments, the microparticles comprise a second polymeric coating on the first polymeric coating, which is formed from a second polymer-forming solution, and which is permeable to the active pharmaceutical ingredient during the sustained-release period. The second polymeric coating can be substantially degraded before or after the first polymeric coating but, like the first polymeric coating, should remain permeable throughout the sustained-release period. If the permeability of the second polymeric coating to the active pharmaceutical ingredient is less than that of the first polymeric coating, it will act as the rate-controlling coating for determining the rate of release. If the permeability of the second polymeric coating is greater, it will function primarily to provide additional mechanical support of protection to the first polymeric coating.

In other embodiments, the microparticles comprise a porous second polymeric coating on the first polymeric coating, which is formed from a second polymer-forming solution, which defines pore regions which permit fluid communication between a pore portion of the first polymeric coating and the external environment, and which defines non-pore regions which prevent fluid communication between a non-pore portion of the first polymeric coating and the external environment. The pores allow diffusion of the active pharmaceutical ingredient across the first polymeric coating in the pore regions, whereas the non-pore region of the second polymeric coating inhibits diffusion of the active pharmaceutical ingredient in the non-pore region. In these embodiments, the second polymeric coating can be substantially impermeable to the active pharmaceutical ingredient in the non-pore regions. By limiting diffusion of the active pharmaceutical ingredient across the first polymeric coating to only the pore regions, the second polymeric coating can reduce the overall rate of release. Moreover, by varying the size of the pore regions, the rate of release can be varied to desired levels. This can be accomplished by including pore-forming agents in the second polymeric coating, and by varying either the identity of the concentration of the pore-forming agents to achieve the desired porosity and, consequently, the desired rate of release.

Microparticle Dimensions and Composition.

As noted above, the coated microparticles of the invention are intended for parenteral administration. In some embodiments the administration will be by injection (e.g., subcutaneous, intravenous, intramuscular, intraocular), although the coated microparticles also can be introduced to a wound site or during surgery (e.g., lavage or irrigation of a wound or surgical site). In all embodiments, the coated microparticles are sufficiently small to form a suspension and, in some embodiments, the microparticles are sufficiently small for injection through a hypodermic needle. Thus, in some embodiments, the coated microparticles have a maximum dimension of between 20 µm and 800 µm, between 40 µm and 400 µm, or between 100 µm and 250 µm.

In addition, in contrast to prior art sustained-release particle formulations, the core particles of the present invention constitute a substantially larger portion of the overall volume and weight of the coated microparticles and, conversely, the polymeric coating(s) constitute a substantially smaller portion. This is advantageous because the overall volume of microparticles which must be administered per unit weight of the active pharmaceutical ingredient is reduced relative to the prior art particles in which the active pharmaceutical ingredient is dissolved or interspersed in a relatively large volume and weight of polymeric matrix material which releases the active pharmaceutical ingredient as it degrades. This advantage arises from the different mechanism of action of the coated microparticles of the invention, in which a relatively thin polymeric coating can contain a relatively large core which contains a saturated solution of the active pharmaceutical ingredient and permits release by diffusion with pseudo-zero-order kinetics.

Thus, in some embodiments, the weight of the polymeric coating(s) is between 0.1% and 200% of the weight of the core particle, or between 2% and 60% of the weight of the core particle. Similarly, in some embodiments, the volume of the polymeric coating(s) is between 0.1% and 200% of the volume of the core particle, or between 2% and 60% of the volume of the core particle.

Polymeric Coatings.

Standard biocompatible and biodegradable polymeric coatings known in the art can be employed in the present invention to the extent that they meet the requirements described above with respect to retaining permeability and/or structural integrity during the desired sustained-release period. The desired sustained-release period can, of course, vary with disease or condition being treated, the nature of the active pharmaceutical ingredient, and the condition of the particular subject to be treated. Thus, the desired sustained-release period can be determined by the attending physician.

The actual sustained-release period for any given preparation of coated microparticles will depend upon various parameters of the microparticles and the route of administration. For example, the sustained-release period will vary depending upon the solubility of the active pharmaceutical ingredient, the rate of clearance of the active pharmaceutical ingredient from the intended site of administration, the size of the core particle and/or the amount of the active pharmaceutical ingredient initially present in the core particle, the presence of other compounds within the core particle that affect the rate of release of the active pharmaceutical ingredient, the permeability of the polymeric coating(s) to the active pharmaceutical ingredient, and the rate of degradation of the polymeric coating(s), as well as other factors.

As is known in the art, both the permeability and biodegradability of polymeric coatings can be affected by the choice of polymeric material (e.g., degree of hydrophobicity or hydrophilicity relative to the active pharmaceutical ingredient; degree of lability of bonds under physiological conditions), degree of cross-linking and thickness. For co-polymers, the ratio of the different monomers also can be varied to affect permeability and biodegradability. With respect to second polymeric coatings which are impermeable to the active pharmaceutical ingredient, pore-forming agents can be used to create pores for fluid communication with the first polymeric coating and, by varying the area of the first polymeric coating which is accessible to the external environment, the average or effective overall permeability of the coated microparticles can be varied.

Examples of frequently used and commercially available biocompatible and biodegradable polymers include poly (lactic acid) (PLA), poly(glycolic acid) (PGA), poly(lactic-co-glycolic acid) (PLGA), poly($\epsilon$-caprolactone) (PCL), poly (valerolactone) (PVL), poly($\epsilon$-decalactone) (PDL), poly(1, 4-dioxane-2,3-dione), poly(1,3-dioxane-2-one), poly(para-dioxanone) (PDS), poly(hydroxybutyric acid) (PHB), poly (hydroxyvaleric acid) (PHV), and poly($\beta$-malic acid) (PMLA).

More generally, useful polymers include, without limitation, naturally occurring polymers including carbohydrates such as sugar phosphates, alkylcelluloses (e.g., ethylcellulose), and hydroxyalkylcelluloses (e.g., hydroxypropylcellulose); and synthetic polymers or co-polymers including one or more of the following monomers: lactic acid, glycolic acid, $\beta$-propiolactone, $\beta$-butyrolactone, $\gamma$-butyrolactone, pivalolactone, $\alpha$-hydroxy butyric acid, $\alpha$-hydroxyethyl butyric acid, $\alpha$-hydroxy isovaleric acid, $\alpha$-hydroxy-$\beta$-methyl valeric acid, $\alpha$-hydroxy caproic acid, $\alpha$-hydroxy isocaproic acid, $\alpha$-hydroxy heptanic acid, $\alpha$-hydroxy octanic acid, $\alpha$-hydroxy decanoic acid, $\alpha$-hydroxy myristic acid, $\alpha$-hydroxy stearic acid, $\alpha$-hydroxy lignoceric acid, $\beta$-phenol lactic acid and polyvinyl alcohol.

Co-polymers offer a degree of flexibility in selecting or designing polymeric coatings with desired properties of permeability and biodegradability because these properties can be controlled by varying the types and relative ratios of co-monomers used. For example, PLGA polymers are more hydrophlic than PLA polymers, and the hydrophilicity can be increased by increasing the percentage of glycolic acid in the co-polymer. On the other hand, PLGA polymers are more rapidly degraded than PLGA polymers, and the rate of degradation can be decreased by increasing the percentage of lactic acid in the co-polymer. As known to those of skill in the art, by varying the types and relative ratios of these and other monomers, polymeric coatings with the desired characteristics can be produced.

In order to affect permeability and/or degradation rates, the polymeric coatings can optionally be covalently or ionically cross-linked. For example, monomers can be chosen which include chemical groups which are capable of forming additional bonds between monomers, or separate cross-linking agents can be included in the polymer-forming solutions in addition to the monomers. In some embodiments, the cross-linking groups are thermally activated, whereas in other embodiments they are photoactivated, including photoactivation by visible or ultraviolet radiation. Cross-linking groups include, without limitation, unsaturated groups such as vinyl, allyl, cinnamate, acrylate, diacrylate, oligoacrylate, methacrylate, dimethacrylate, and oligomethoacrylate groups.

Because many active pharmaceutical ingredients are hydrophobic, and because it is desirable to reduce or avoid dissolution of the active pharmaceutical ingredient in the first polymeric coating, some embodiments of the invention employ a hydrophilic polymer as the first polymeric coating. Examples of hydrophilic polymeric coatings include, without limitation, poly(vinyl alcohol) (PVA), poly(ethylene glycol) (PEG), poly(ethylene oxide), poly(vinylpyrrolidone), poly(ethyloxazoline), or polysaccharides or carbohydrates such as alkylcelluloses, hydroxyalkylcelluloses, hyaluronic acid, dextran, heparan sulfate, chondroitin sulfate, heparin, or alginate, or proteins such as gelatin, collagen, albumin, ovalbumin, or polyamino acids.

For active pharmaceutical ingredients which are hydrophilic, some embodiments of the invention employ a hydrophobic polymer as the first polymeric coating. Examples of hydrophobic polymers include, without limitation, PLA, PGA, PLGA, PCL, poly(allylene oxides), polyanhydrides (see, e.g., U.S. Pat. No. 4,757,128, U.S. Pat. No. 4,857,311, U.S. Pat. No. 4,888,176, and U.S. Pat. No. 4,789,724) and co-polymers thereof.

As noted above, in some embodiments, a second polymeric coating is employed which is impermeable to the active pharmaceutical ingredient but which includes pores through which the first polymeric coating is accessible to the external environment and through which the active pharmaceutical ingredient can be released. Therefore, in such embodiments, the second polymer-forming solution can comprise pore-forming agents which dissolve after formation of the second polymeric coating (either in vitro prior to administration, or in vivo after administration).

Methods of Forming Polymeric Coatings.

Methods of forming polymeric coatings on particles are well known in the art. For example, standard techniques include solvent evaporation/extraction techniques, in-water drying techniques (see, e.g., U.S. Pat. No. 4,994,281), organic phase separation techniques (see, e.g., U.S. Pat. No. 4,675,19, U.S. Pat. No. 5,639,480), spray-drying techniques (see, e.g., U.S. Pat. No. 5,651,990), triple emulsion techniques (see, e.g., U.S. Pat. No. 4,652,441, U.S. Pat. No. 5,639,480), air suspension techniques, and dip coating techniques.

For example, a PVA polymeric coating can be applied using a dip coating technique. In brief, a 1% solution of PVA in water can be formed by dissolving excess PVA in water at 60° C. for 2 h (see, e.g., Byron and Dalby (1987), *J. Pharm. Sci.* 76(1):65-67). Alternatively, a higher concentration PVA solution (e.g., 3-4%) can be prepared in a reflux with heating to approximately 90-100° C. After cooling, the microparticles can be added to the PVA solution and agitated by, for example, swirling or stirring. The microparticles are then removed from the solution by, for example, filtration on filter paper with a mesh size appropriate to the microparticles. Optionally, vacuum-filtration can be employed to assist in drying. Untreated, PVA polymeric coatings or films are readily permeable to water and hydrophilic drugs. Heating of PVA, however, causes an increase in crystallinity and decrease of permeability of up to 500-fold with increasing temperatures in the range of 100-200° C. for periods of 0-160 hours (Byron and Dalby (1987), supra). Thus, in some embodiments, PVA polymeric coatings can be heated to temperatures between 100° C. and 200° C., between 125° C. and 175° C., or between 155° C. and 170° C. for periods between 1 sec. and 160 hours, between 1 min. and 10 hours, or between 5 minutes and 2 hours. Optionally, the coating process can be repeated several times to build-up a thicker polymeric coating.

For the production of second polymeric coatings including pores, the second polymer-forming solution optionally can include pore-forming agents. Pore-forming agents include, without limitation, compounds such as sugars (e.g., glucose, sucrose, lactose, saccharose) or salts (e.g., sodium chloride), polyalcohols (e.g., glycerol), organic acids (e.g., citric acid, fumaric acid), and polymers such as hydroxypropyl cellulose, hydroxypropylmethyl cellulose, polyethylene glycols, and polyvinyl pyrrolidones, and mixtures thereof. The pore-forming agents can be removed from the coated microparticles prior to administration, or can dissolve in vivo.

Methods of Administration.

The coated microparticles of the invention are administered parenterally. In some embodiments, the administration is by injection of a suspension of the coated microparticles in a pharmaceutically acceptable carrier, whereas in other embodiments the coated microparticles are administered to an open wound or surgical site.

Administration by injection includes, without limitation, subcutaneous, intravenous, intramuscular and intraocular injection. For such routes of administration, the coated microparticles must have a maximum dimension which is less than the inner diameter of the needle used for injection. Although larger needles may be employed to accommodate larger coated microparticles, such larger coated microparticles can have decreased ability to form a suspension. Therefore, in some embodiments, the coated microparticles have a maximum dimension less than the inner diameter of standard needles for parenteral injection. Moreover, the coated microparticles can be chosen to have a maximum size which permits formulation as a suspension in a pharmaceutically acceptable carrier.

For parenteral administration to open wounds or surgical sites, the coated microparticles can be administered in a suspension, as described above, or as a solid (e.g., a powder), paste, cream, or ointment. In such embodiments, the coated microparticles can be administered during lavage or irrigation of a wound or surgical site, and the coated microparticles can be substantially larger.

Active Pharmaceutical Ingredients.

Active pharmaceutical ingredients which may be formulated according to the invention include any active pharmaceutical ingredients or pharmaceutically acceptable salts thereof which may be formulated into coated microparticles of the invention without undergoing chemical alteration or degradation which adversely affects its pharmaceutical utility. One of ordinary skill can easily ascertain whether any given active pharmaceutical ingredient is useful in the present invention by preparing a coated microparticle and comparing the chemical structure of the released form to the known active form. Such active pharmaceutical ingredients can be selected from various groups based on the type of agent or type of condition being treated.

By way of non-limiting examples, potentially useful active pharmaceutical ingredients can be selected from groups including corticosteroids, anti-psychotics, anti-depressants, anti-epileptics, anti-Parkinson agents, anesthetics, narcotics, antibiotics, HIV protease inhibitors, reverse transcriptase inhibitors, HMG CoA reductase inhibitors, calcium channel blockers, β-blockers, angiotensin II receptor antagonists, angiotensin converting enzyme (ACE) inhibitors, taxanes, alkylating agents, immunosuppressive agents, hormones and hormone receptor modulators, as well as other active pharmaceutical ingredients for which sustained-release formulations would be advantageous.

Non-limiting examples of corticosteroids include dexamethasone, triamcinolone, fluocinolone, fluocinolone acetonide, cortisone, prednisolone, fluometholone, clobetasone butyrate, triamcinolone acetonide, betamethasone valerate, diflucortolone valerate, fluticasone valerate, hydrocortisone 17-butyrate, mometasone furoate, methylprednisolone acetonate, clobetasol propionate, betamethasone dipropionate, desonide and fluticasone.

Non-limiting examples of anti-psychotics include benzodiazepines such as olanzapine (Zyprexa™), clozapine, loxapine, and quetiapine; benzisoxazole derivatives such as risperidone (Risperdal™) and molindone, and pimozide.

Non-limiting examples of antidepressants include tertiary amine tricyclics such as amitriptaline, doxepin and imipramine; secondary amine tricyclics such as desipramine and nortrypitylene; tetracyclics such as mirtazapine; triazolopyridines such as trazadole; aminoketones such as buproprion; phenethylamines such as venlafaxine; phenylpiperazines such as nefazadone; and selective serotonin reuptake inhibitors (SSRIs) such as citalopram, fluoxetine, fluvoxamine, paroxetine, and sertaline.

Non-limiting examples of anti-epileptics include hydantoins such as dilantin; barbiturates such as phenobarbital; deoxybarbiturates such as primidone; iminostilbenes such as cabamazepine; succinimides such as ethosuximide; benzodiazepines such as clonazepam; as well as valproic acid, gabapentin, levetiracetam, tiagabine, topiramate and zonisamide.

Non-limiting examples of anti-Parkinson agents include levodopa preparations such as levodopa benserazide and levodopa/carbidopa; ergot dopamine agonists such as bromocriptine, cabergoline, and pergolide; non-ergot dopamine agonists such pramipexole, ropinerole, and spomorphine; catechol-O-methyltransferase inhibitors such as entacapone and tolcapone; monoamine oxidase B inhibitors such as selegiline; NMDA antagonists such as amantadine; and anticholinergics such as benzhexol, benztropine, biperiden, orphenedrine, and procyclidine.

Non-limiting examples of anesthetics include procaine (Novocain™), bupivacaine (Marcaine™), lidocaine (Xylocaine™), etidocaine, ropivacaine, choloroprocaine, tetracaine and mepivacine.

Non-limiting examples of narcotics include morphine, hydromorphone, meperidine, fentanyl, propoxyphene, levorphanol, codeine, hydrocodone, oxymorphone, levomethadyl acetate, oxycodone and methadone.

Non-limiting examples of antibiotics include tetracycline antibiotics, such as tetracycline, chlortetracycline, oxytetracycline, demeclocycline, methacycline, doxycycline, and minocycline; penicillin antibiotics such as penicillin, chlorpenicillin, oxypenicillin, methicillin, nafcillin, oxacillin, cloxacillin, dicloxacillin, ampicillin, amoxicillin, bacampicillin, carbenicillin, carbenicillin indanyl, ticarcillin, mezlocillin and piperacillin; macrolide antibiotics such as erythromycin, clarithromycin and azithromycin; fluoroquinolone antibiotics such as norfloxacin, ciprofloxacin, ofoxacin, sparfloxacin, lomefloxacin, fleroxacin, perfloxacin, levofloxacin, trovafloxacin, gatifloxacin, moxifloxacin and cloxacillin; cephalosporin antibiotics such as cephalothin, cefazolin, cephalexin, cefadroxil, cefamanadole, cefoxitin, cefaclor, cefuroxime, cefuroxime axetil, loracarbef, cefonicid, cefatetan, ceforanide, cefotaxime, cefpodoxime proxetil, ceftriaxone, cefoperazone, ceftazidime and cefepime; aminoglycoside antibiotics include gentamicin, tobramycin, amikacin, netilimicin, neomycin, kanamycin, streptomycin, dactinomycin, daunorubicin, bleomycin, plicamycin, and mitomycin; as well as isoniazid (INH), rifampin, rifapentine, pyrazinamide, ethambutol, ethionamide, careomycin and cycloserine.

Non-limiting examples of HIV protease inhibitors include ritonavir, indinavir, nelfinavir, saquinavir, amprenavir and lopinavir.

Non-limiting examples of nucleoside reverse transcriptase inhibitors include the nucleoside-based reverse transcriptase inhibitors zidovudine, didanosine, stavudine, zalcitabine, lamuvidine, and abacavir, and the non-nucleoside-based reverse transcriptase inhibitors include delavirdine, efavirenez and nevirapine.

Non-limiting examples of HMG Co-A reductase inhibitors include simvastatin (Zocor™), lovastatin (Mevacor™), atorvastatin (Lipitor™), pravastatin sodium, fluvastatin and cerivastatin Non-limiting examples of calcium channel blockers include dihydropyridines, such as nifedipine; phenyl alkyl amines, such as verapamil; and benzothiazepines, such as diltiazem; as well as amrinone, amlodipine, bencyclane, felodipine, fendiline, flunarizine, isradipine, nicardipine, nimodipine, perhexilene, gallopamil, tiapamil, phenyloin, barbiturates, dynorphin, omega-conotoxin, and omega-agatoxin.

Non-limiting examples of β blockers include propranolol, atenolol, acebutolol, alprenolol, befunolol, betaxolol, bunitrolol, carteolol, celiprolol, hedroxalol, indenolol, labetalol, levobunolol, mepindolol, methypranol, metindol, metoprolol, metrizoranolol, oxprenolol, pindolol, practolol, sotalolnadolol, tiprenolol, tomalolol, timolol, bupranolol, penbutolol and trimepranol.

Non-limiting examples of angiotensin II receptor antagonists include saralasin.

Non-limiting examples of ACE inhibitors captopril, zofenopril, enalapril, lisinopril, quinapril, ramipril, perindopril, cilazapril, benazapril, fosinopril and trandolopril.

Non-limiting examples of taxanes include paclitaxel and docetaxel.

Non-limiting examples of alkylating agents include the nitrogen mustards, alkyl sulfonate, nitrosurea, ethylenimine and methylmelamine, triazene classes, cyclophosphamide, ifosamide, thiotepa, melphalan, busulfan, carmustine, clorambucil, hexamethylmelamine and streptozocin.

Non-limiting examples of immunosuppressive agents that suppress the immune system includes the corticosteroids, the purine antagonists such as azathioprine, cyclosporine, tacrolimun, sirolimus and mycophenolate mofetil.

Non-limiting examples of hormones and hormone receptor modulators include insulin, pituitary growth hormone, adrenocorticotrophic hormone, testosterone, progesterone, estrogen, levonorgestrel (Norplant™), tamoxifen, raloxifen and fulvestrant.

Non-limiting examples of other active pharmaceutical ingredients potentially useful in the invention include vinca alkaloids such as vincristine and vinblastine; platinum coordination complexes such as cisplatin and carboplatin; isoflavones such as genistein, formomonetin, daidzein and equol; epidophylotoxins such as etoposide and teniposide; camptothecins such as topotecan, and iritecan; folic acid analogues such as methotrexate; pyrimidine analogues such as 5-fluorouracil, floxuridine, and cytosine arabinoside; and purine analogues such as 6-mercaptopurine, 6-thioguanine, and 2-deoxycoformycin; as well as the anti-alcoholism medication disulfiram (Antabuse™).

The following examples illustrate some specific modes of practicing the present invention, but are not intended to limit the scope of the claimed invention. Alternative materials and methods may be utilized to obtain similar results.

EXAMPLES

Formation of Core Particle

Pressure-fused particles were prepared from the active pharmaceutical ingredient olanzapine, an atypical antipsychotic drug, obtained in micronized form (90% of particles<5 μm in diameter) from a commercial supplier (Dr. Reddy Labs, Upper Saddle River, N.J.). The lower punch of a hydraulic press used for producing IR pellets was placed into a die with an 8 mm diameter, and approximately 30 mg of olanzapine was loaded into the die. The upper punch was placed into the die, and moderate pressure was applied by hand to pack and evenly distribute the active pharmaceutical ingredient in the die. The die assembly was seated in the press and force was increased to 25-30 mtons and maintained for a minimum of 30 seconds, and typically 90 seconds. Given that the die had a diameter of 8 mm, the area of the die was approximately 0.50 $cm^2$ and, therefore, the pressure was 50-60 mtons/$cm^2$. Alternatively, given that 1 giga-Pascal (GPa) is equal to 10.197 mtons/$cm^2$, the pressure was approximately 5-6 GPa.

The high pressure compaction produced a "fused" or "glassy" wafer of olanzapine that was removed from the press. The compacted sample was then forced through a 60 mesh sieve grating with apertures of approximately 250 μm to produce roughly cuboidal particles.

Formation of PVA First Polymeric Coating.

Polyvinyl alcohol (PVA) was obtained with a mol. wt. range of 124,000. Excess PVA was heated in water at 65° C. After cooling, the PVA solution was decanted and mixed with core particles prepared as described above. The core particles were swirled in a beaker of the PVA solution for several seconds, and vacuum-filtered onto #42 filter paper (Whatman, Inc., Clifton, N.J.) in a 9 cm diameter Buchner funnel. The filter paper with retained coated core particles was transferred to a watch glass and dried at 155° C. or 165° C. for 10 minutes. This process was repeated 4-5 times.

Dissolution Testing.

The dissolution of micronized olanzapine (90% of particles<5 μm in diameter) from a commercial supplier (Dr. Reddy Labs, Upper Saddle River, N.J.) was compared with the dissolution of coated microparticles of olanzapine prepared as described above.

Powder dissolution testing was carried out in distilled water at 25° C. A 2-3 mg sample of the powder in 25 ml of water was 50% dissolved at approximately 1 minute, and was completely dissolved in 2.5 minutes.

Figure 1:
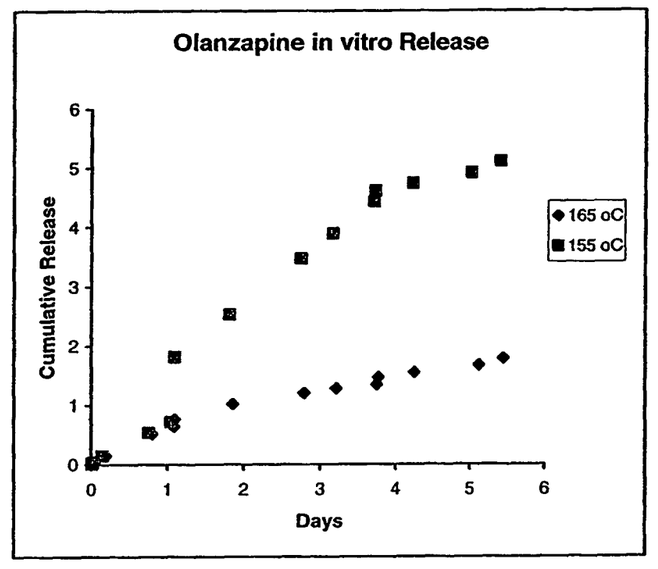
FIG. 1 presents data regarding the release of an active pharmaceutical ingredient from coated microparticles of the invention over a sustained-release period.

Coated microparticle dissolution testing was also carried out in distilled water at 25° C. A 2-3 mg sample was placed in 25 ml of water. The microparticles were completely covered by the solution. Every 24 h for 5 days, 5 ml of the supernatant solution was carefully removed and replaced with fresh media, avoiding mixing of the buffer, to simulate physiological "sink" conditions. FIG. 1 represents the data regarding the release of the active pharmaceutical ingredient from the coated microparticles over time. As shown in the FIGURE, the rate of release was substantially constant or pseudo-zero-order over several days. The release rate from the PVA-coated microparticles dried at the lower temperature was greater, indicating that drying temperature can be used to vary permeability and release rate.

Active Pharmaceutical Ingredient Stability.

To determine whether the formation of the core particles or polymeric coatings altered or degraded the active pharmaceutical ingredient, high performance liquid chromatography (HPLC) was employed. An HP 1050 HPLC System chromatograph (Agilent Technologies, Palo Alto, Calif.) with variable wavelength detector was used with a silica HPLC column (Grace Vydac, Inc., Columbia, Md., Product #101TP54) with normal phase (unbonded), 300 Å pore size, 5 μm particle size, 4.6 mm×250 mm. The injection volume was 20 μl, with a flow rate of 1.0 ml/min at 25° C. (ambient). The pump was operated in isochratic mode, the post time was 3.0 minutes, and absorbance at 254 nm was measured. The mobile phase was 50:50 chloroform:isooctane.

The samples were taken from the dissolution tests described above. HPLC analysis performed confirmed the purity of the olanzapine from the coated microparticles of the invention and the absence of breakdown products.

EQUIVALENTS

While this invention has been particularly shown and described with references to specifics embodiments thereof, it will be understood by those skilled in the art that various changes in form and details may be made therein without departing from the spirit and scope of the invention as defined by the appended claims. Those skilled in the art will recognize, or be able to ascertain using no more than routine experimentation, many equivalents to the specific embodiments of the invention described specifically herein. Such equivalents are intended to be encompassed in the scope of the appended claims.

What is claimed is:

1. A pharmaceutical preparation for sustained-release of an active pharmaceutical ingredient after parenteral administration comprising:
   a multiplicity of coated microparticles, said coated microparticles having a mean dimension of less than 1 mm and each coated microparticle comprising
   (a) a core particle consisting of said active pharmaceutical ingredient; and
   (b) a first polymeric coating enveloping said core particle;
   wherein said first polymeric coating is crystalline and is permeable to water and said active pharmaceutical ingredient while maintaining structure integrity during a sustained-release period from administration of said microparticles.

2. The pharmaceutical preparation of claim 1, wherein diffusion of said active pharmaceutical ingredient across said first polymeric coating exhibits pseudo-zero-order kinetics during said sustained-release period.

3. The pharmaceutical preparation of claim 1, wherein said first polymeric coating is substantially degraded after said sustained-release period.

4. The pharmaceutical preparation of claim 1, wherein said microparticles are administrable via parenteral injection.

5. The pharmaceutical preparation of claim 4, wherein said microparticles have a maximum dimension between 20 μm and 800 μm.

6. The pharmaceutical preparation of claim 4, wherein said microparticles have a maximum dimension between 40 μm and 400 μm.

7. The pharmaceutical preparation of claim 4, wherein said microparticles have a maximum dimension between 100 μm and 250 μm.

8. The pharmaceutical preparation of claim 1, wherein the first polymeric coating is formed by coating the core particle of said active pharmaceutical ingredient in a first polymer-forming solution, and wherein the core particle is substantially insoluble in said first polymer-forming solution.

9. The pharmaceutical preparation of claim 8, wherein said active pharmaceutical ingredient is hydrophobic and said first polymer-forming solution is hydrophilic.

10. The pharmaceutical preparation of claim 8, wherein said active pharmaceutical ingredient is hydrophilic and said first polymer-forming solution is hydrophobic.

11. The pharmaceutical preparation of claim 1, further comprising:
(c) a second polymeric coating on said first polymeric coating;
wherein said second polymeric coating is permeable to said active pharmaceutical ingredient during said sustained-release period.

12. The pharmaceutical preparation of claim 1, further comprising:
(c) a porous second polymeric coating on said first polymeric coating;
wherein said second polymeric coating defines pore regions which permit fluid communication between a pore portion of said first polymeric coating and an external environment, thereby allowing diffusion of said active pharmaceutical ingredient across said first polymeric coating in said pore regions; and
wherein said second polymeric coating defines non-pore regions which prevent fluid communication between a non-pore portion of said first polymeric coating and an external environment, thereby inhibiting diffusion of said active pharmaceutical ingredient across said first polymeric coating in said non-pore regions.

13. The pharmaceutical preparation of claim 12, wherein said second polymeric coating is substantially impermeable to said active pharmaceutical ingredient in said non-pore regions.

14. The pharmaceutical preparation of claim 12, wherein said second polymer-forming solution comprises pore-forming agents which dissolve to produce said pore regions after formation of said second polymeric coating.

15. The pharmaceutical preparation of claim 1, wherein said first polymeric coating comprises a polymer or co-polymer including at least one monomer selected from the group consisting of sugar phosphates, alkylcellulose, hydroxyalkylcelluloses, lactic acid, glycolic acid, β-propiolactone, β-butyrolactone, γ-butyrolactone, pivalolactone, α-hydroxy butyric acid, α-hydroxyethyl butyric acid, α-hydroxy isovaleric acid, α-hydroxy-β-methyl valeric acid, α-hydroxy caproic acid, α-hydroxy isocaproic acid, α-hydroxy heptanic acid, α-hydroxy octanic acid, α-hydroxy decanoic acid, α-hydroxy myristic acid, α-hydroxy stearic acid, α-hydroxy lignoceric acid, β-phenol lactic acid and polyvinyl alcohol.

16. The pharmaceutical preparation of claim 11 or 12, wherein said second polymeric coating comprises a polymer or co-polymer including at least one monomer selected from the group consisting of sugar phosphates, alkylcellulose, hydroxyalkylcelluloses, lactic acid, glycolic acid, β-propiolactone, β-butyrolactone, γ-butyrolactone, pivalolactone, α-hydroxy butyric acid, α-hydroxyethyl butyric acid, α-hydroxy isovaleric acid, α-hydroxy-β-methyl valeric acid, α-hydroxy caproic acid, α-hydroxy isocaproic acid, α-hydroxy heptanic acid, α-hydroxy octanic acid, α-hydroxy decanoic acid, α-hydroxy myristic acid, α-hydroxy stearic acid, α-hydroxy lignoceric acid, β-phenol lactic acid and polyvinyl alcohol.

17. The pharmaceutical preparation of claim 1, wherein said first polymeric coating is applied to said core particles by an air suspension technique.

18. The pharmaceutical preparation of claim 1, wherein said first polymeric coating is applied to said core particles by a dip coating technique.

19. The pharmaceutical preparation of claim 1, wherein the weight of said first polymeric coating is between 0.1% and 200% of the weight of said core particle.

20. The pharmaceutical preparation of claim 1, wherein the weight of said first polymeric coating is between 2% and 60% of the weight of said core particle.

21. The pharmaceutical preparation of claim 1, wherein the volume of said first polymeric coating is between 0.1% and 200% of the volume of said core particle.

22. The pharmaceutical preparation of claim 1, wherein the volume of said first polymeric coating is between 2% and 60% of the volume of said core particle.

23. A method of sustained-release administration of an active pharmaceutical ingredient comprising administering parenterally a pharmaceutical preparation of claim 1 in the form of a suspension of said coated microparticles in a pharmaceutically acceptable carrier.

24. The method of claim 23, wherein said parenteral administration is selected from the group consisting of subcutaneous, intravenous, intramuscular and intraocular injection.

25. A pharmaceutical preparation for sustained-release of an active pharmaceutical ingredient after parenteral administration comprising:
a multiplicity of coated microparticles, said coated microparticles having a mean dimension of less than 1 mm and each coated microparticle comprising
(a) a core particle consisting of said active pharmaceutical ingredient; and
(b) a first polymeric coating enveloping said core particle;
wherein said active pharmaceutical ingredient forms a saturated solution within said coated microparticles after said administration;
wherein said first polymeric coating is crystalline and is permeable to said active pharmaceutical ingredient during a sustained-release period from administration of said microparticles until the concentration of said active pharmaceutical ingredient contained within said microparticles is unsaturated; and
wherein the weight of the first polymeric coating is between 2% and 60% of the weight of the core particle.

26. A pharmaceutical preparation for sustained-release of an active pharmaceutical ingredient after parenteral administration comprising:
a multiplicity of coated microparticles, said coated microparticles having a mean dimension of less than 1 mm and each coated microparticle comprising (a) a core particle consisting of said active pharmaceutical ingredient; and
(b) a first polymeric coating enveloping said core particle;
wherein said active pharmaceutical ingredient forms a saturated solution within said coated microparticles after said administration;
wherein said first polymeric coating is crystalline and is permeable to said active pharmaceutical ingredient during a sustained-release period from administration of said microparticles until the concentration of said active pharmaceutical ingredient contained within said microparticles is unsaturated; and
wherein the volume of the first polymeric coating is between 2% to 60% of the volume of the core particle.

27. A pharmaceutical preparation for sustained-release of an active pharmaceutical ingredient after parenteral administration comprising:
a multiplicity of coated microparticles, said coated microparticles having a mean dimension of less than 1 mm and each coated microparticle comprising
(a) a core particle consisting of said active pharmaceutical ingredient; and
(b) a first polymeric coating enveloping said core particle;
wherein said active pharmaceutical ingredient forms a saturated solution within said coated microparticles after said administration;
wherein said first polymeric coating is crystalline and is permeable to said active pharmaceutical ingredient during a sustained-release period from administration of said microparticles until the concentration of said active pharmaceutical ingredient contained within said microparticles is unsaturated; and
wherein the sustained-release period is at least five days.

28. A pharmaceutical preparation of claim 1 wherein the active pharmaceutical ingredient is in the form of single crystal, a multiplicity of crystals, macrocrystal, or pressure-fused particle.

* * * * *